US00PP13501P2

(12) United States Plant Patent
Zaiger et al.

(10) Patent No.: US PP13,501 P2
(45) Date of Patent: Jan. 21, 2003

(54) NECTARINE TREE NAMED 'ZEE FIRE'

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 10/045,763

(22) Filed: Jan. 15, 2002

(51) Int. Cl.[7] ..... A01H 5/00
(52) U.S. Cl. ..... Plt./190
(58) Field of Search ..... Plt./190

*Primary Examiner*—Bruce R. Campell
*Assistant Examiner*—Anne Marie Grünberg

(57) ABSTRACT

A new and distinct variety of nectarine tree (*Prunus persica* var. *nucipersica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices such as pruning, thinning, spraying, irrigation and fertilization. Its novelty consists of the following unique combination of features that are desirable in a new variety.

1. Heavy and regular production of fruit.
2. Fruit maturing in the early maturing season.
3. Fruit with good handling and shipping quality.
4. Fruit with attractive red skin color.
5. Fruit with good flavor and eating quality.
6. Vigorous, upright growth of tree.

1 Drawing Sheet

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of nectarine tree (*Prunus persica* var. *nucipersica*) was originated and asexually reproduced by us in our experimental orchard located near Modesto, Stanislaus County, Calif.

PRIOR VARIETIES

Among the existing varieties of peaches and nectarines, which are known to us, and mentioned herein, are 'Tasty Gold' Nectarine (U.S. Plant Pat. No. 5,623), 'May Glo' Nectarine (U.S. Plant Pat. No. 5,245), 'Fayette' Peach (non-patented), 'May Crest' Peach (U.S. Plant Pat. No. 4,064) and 'May Grand' Nectarine (U.S. Plant Pat. No. 2,794).

STATEMENT REGARDING FEDERALLY SPONSORED RESEARCH AND DEVELOPMENT

Not applicable.

ORIGIN OF THE VARIETY

The present new variety of nectarine tree (*Prunus persica* var. *nucipersica*) was originated by us in our experimental orchard located near Modesto, Calif., as a first generation cross between proprietary lines of the immediate parents with identification numbers 172LE506 and 201LF103. The maternal parent 172LE506 originated from crosses derived from 'Tasty Gold' Nectarine (U.S. Plant Pat. No. 5,623) with 'May Glo' Nectarine (U.S. Plant Pat. No. 5,245). The pollen parent 201LF103 originated from crosses between the following, 'Fayette' Peach (non-patented), 'May Grand' Nectarine (U.S. Plant Pat. No. 2,794) and 'May Crest' Peach (U.S. Plant Pat. No. 4,064). In 1995, we budded a large group of these first generation seedlings to 'Nemaguard'Rootstock (non-patented) and, under close and careful observation; we selected the present variety, which exhibited exceptional fruit characteristics, for additional asexual propagation and commercialization.

ASEXUAL REPRODUCTION OF THE VARIETY

Additional asexual reproductions in 1997 of the new and distinct variety of nectarine tree was by budding to 'Nemaguard' Rootstock (non-patented), the standard rootstock for peaches and nectarines in California, as performed by us in our experimental orchard located near Modesto, Calif., and shows that asexual reproductions run true to the original tree and all characteristics of the tree and its fruit are established and transmitted through succeeding asexual propagations.

SUMMARY OF THE NEW VARIETY

The present variety of nectarine tree (*Prunus persica* var. *nucipersica*) is of large size, vigorous, upright growth and a productive and regular bearer of large, yellow flesh, clingstone fruit ripening in the early maturity season with good flavor and eating quality. The fruit is further characterized by having an attractive red skin color, having firm flesh with good storage and shipping quality and holding firm on the tree 5 to 7 days after maturity (shipping ripe). The tree is further characterized by having a low winter chilling requirement of approximately 300 hours below 45° F., allowing this variety to be grown in more southern areas than most commercial varieties. In comparison to 'Tasty Gold' Nectarine (U.S. Plant Pat. No. 5,623), the fruit of the new variety is approximately 2 weeks earlier in maturity, the tree has a lower winter chilling requirement by approximately 500 hours, allowing it to produce fruit in more southern areas of early maturity. In comparison to 'May Glo'

Nectarine (U.S. Plant Pat. No. 5,245), the fruit of the new variety is slightly larger in size and 6 days earlier in maturity.

PHOTOGRAPH OF THE NEW VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the 5 year old, new variety of nectarine tree, its flowers, foliage and fruit, as based on observations of specimens grown near Modesto, Calif., in accordance with Munsell Book of Color.

Tree:

*Size.*—Large, normal for nectarine trees. Height controlled by pruning to 3 to 3.5 meters for economical harvesting of fruit.

*Vigor.*—Vigorous. Growth of 1.5 to 2 meters the first growing season. Usually pruned to 1 to 1.5 meters in height in the first dormant season when primary scaffolds are selected.

*Growth.*—Upright. Normal for nectarine trees.

*Branching habit.*—Upright with crotch angle at approximately 30 to 35°. At maturity, branch angle increases with weight of fruit.

*Productivity.*—Productive. Produces 1.5 to several times the number of fruit desired for crop load. Number of fruit set varies with climatic conditions during blooming season. Thinning and spacing of fruit necessary.

*Bearer.*—Regular. Adequate set 4 consecutive years. No alternate bearing observed.

*Fertility.*—Self fertile, abundant pollen.

*Density.*—Medium dense. Usually pruned to vase shape by removing branches from center of tree to allow more sunlight and air movement to enhance fruit color and health of fruit wood.

*Hardiness.*—Hardy in all stone fruit areas of California. Grown in USDA Hardiness Zone 9.

Trunk:

*Size.*—Medium to large, stocky. Average circumference 50.8 cm at 27.94 cm above ground on a 5 year old tree.

*Surface texture.*—Medium shaggy. Roughness increases with age.

*Color.*—Varies from 10R 7/1 to 10YR 7/1.

Branches:

*Size.*—Medium, normal for nectarine trees. Average circumference 1.61 cm at 1½ meters above ground. Crotch angle approximately 30° to 35°, increases with crop load.

*Surface texture.*—Smooth on new growth. Medium rough on old growth.

*Lenticels.*—Average number of 43 in a 25.8 square cm section. Average length 4.3 mm. Average width 1.7 mm. Color 7.5YR 6/10 to 7.5YR 5/10.

*Color.*—New growth 5GY 7/6 to 5GY 7/8. Old growth 7.5YR 3/4 to 7.5YR 4/4.

Leaves:

*Size.*—Medium to large. Average length 111.4 mm. Average width 37.2 mm.

*Form.*—Lanceolate.

*Margin.*—Crenate.

*Thickness.*—Medium.

*Surface texture.*—Upper surface relatively smooth except for small indentation over veining, glabrous. Lower surface relatively smooth except for small ridges created by midrib and pinnate venation, glabrous.

*Petiole.*—Average length 9.1 mm. Average width 1.6 mm. Color — 2.5GY 5/6. Grooved longitudinally. Pubescence — wanting.

*Glands.*—Reniform. Large size. Average length 1.2 mm. Average diameter 0.6 mm. Number varies from 2 to 3, average number 2. Located on upper portion of leaf petiole and base of leaf blade. Color — 2.5GY 7/8.

*Color.*—Upper surface 5GY 4/4. Lower surface 5GY 5/4.

*Midvein.*—Color — 2.5GY 8/6.

*Apex.*—Acuminate.

*Base.*—Cuneate.

Flower buds:

*Size.*—Large. Average length 16.1 mm. Average width 8.7 mm.

*Hardiness.*—Hardy in all stone fruit growing areas of California.

*Form.*—Plump, conical, becoming elongated before opening.

*Pedicel.*—Average length 2 mm. Average width 1.6 mm. Color 2.5GY 8/10.

*Color.*— 7.5RP 8/6.

Flowers:

*Size.*—Large, showy. Average height 18.9 mm. Average diameter 44 mm.

*Petals.*—Large. Average length 20.1 mm. Average width 18.2 mm. Number — 5, alternately arranged to sepals. Shape — orbicular, narrows at point of attachment. Margin — sinuate. Color — 2.5RP 8/6.

*Sepals.*—Number — 5, alternately arranged to petals. Average length 3.6 mm. Average width 2.5 mm. Shape — ovate, apex rounded. Color — upper surface 2.5GY 7/10, glabrous. Lower surface 7.5RP 3/8, pubescent.

*Stamens.*—Average number per flower 40. Average filament length 14.1 mm. Filament color varies from 5RP 9/2 to 5RP 5/12. Anther color 3.75R 4/14, becoming more yellow with age.

*Pollen.*—Self fertile. Color 8.75YR 7/12.

*Pistil.*—Number — one. Average length 14.9 mm. Stigma approximately 1.9 mm above anthers. Color 2.5GY 9/6. Pubescence — wanting.

*Fragrance.*—Slight.

*Blooming period.*—Date of First Bloom Feb. 12, 2001. Date of Last Bloom Feb. 27, 2001. Varies slightly with climatic conditions.

*Color.*—2.5RP 8/6.

*Number of flowers per flower bud.*—One.

*Pedicel.*—Average length 2 mm. Average width 1.7 mm. Color 2.5GY 8/10.

Fruit:

*Maturity when described.*—Firm ripe.

*Date of first picking.*—May 20, 2001.

*Date of last picking.*—May 26, 2001. Varies slightly with climatic conditions.

*Size*.—Average diameter axially 69.2 mm. Average transversely in suture plane 70.3 mm. Average weight 150.5 grams. Average weight varies slightly with fertility of the soil, amount of thinning and climatic conditions.

*Form*.—Usually globose, varies from globose to slightly concaved on one side near the apex on some fruit.

*Suture*.—Shallow, extends from base to apex.

*Ventral surface*.—Nearly smooth.

*Apex*.—Usually rounded. Varies from rounded to slightly retuse.

*Base*.—Retuse.

*Cavity*.—Rounded to slightly elongated in the suture plane. Average depth 4.7 mm. Average breadth 12.5 mm.

Stem:

*Size*.—Average length 5.2 mm. Average diameter 3.1 mm.

*Color*.—2.5GY 7/8 to 2.5GY 7/10.

Flesh:

*Ripens*.—Evenly.

*Texture*.—Firm, meaty.

*Fibers*.—Few, small, tender.

*Firmness*.—Good. Firmer than most early maturing commercial varieties.

*Aroma*.—Slight.

*Amydgalin*.—Undetected.

*Eating quality*.—Good.

*Flavor*.—Good. Good balance between sugar and acid.

*Juice*.—Moderate, enhances flavor.

*Brix*.—Soluble solids 13.7° Brix. Varies slightly with amount of fruit per tree and climatic conditions.

*Color*.—2.5Y 8/8 to 2.5Y 8/10. Pit cavity varies from 2.5Y 7/8 to 2.5Y 7/10.

Skin:

*Thickness*.—Medium, normal compared to most commercial nectarine varieties.

*Texture*.—Smooth, no waffling or roughness.

*Pubescence*.—Wanting.

*Tendency to crack*.—Very slight in high moisture conditions.

*Color*.—Ground color 3.75Y 8.5/12 to 3.75Y 8/12. Nearly overspread with 7.5R 3/10 to 7.5R 4/14. Small randomly spaced areas of ground color showing, leaving a speckling pattern around apex.

*Tenacity*.—Tenacious to the flesh.

*Astringency*.—Undetected.

Stone:

*Type*.—Clingstone.

*Size*.—Large. Average length 33.4 mm. Average width 26.0 mm. Average thickness 21.4 mm.

*Form*.—Ovate.

*Base*.—Rounded.

*Apex*.—Varies from round to acute. Short, average length 1.6 mm.

*Surface*.—Irregularly furrowed toward apex, pitted throughout. Pits vary from round to elongated. Usually one deep furrow on each side of suture.

*Sides*.—Vary from equal to unequal with one side extending further from suture plane.

*Ridges*.—Small to medium in width. Relatively smooth.

*Tendency to split*.—Very slight.

*Color*.—2.5YR 9/4, when dry and clean of flesh.

Kernal:

*Size*.—Average length 15.1 mm. Average width 9.58 mm. Average thickness 5.2 mm.

*Skin color*.—2.5Y 8.5/8.

*Viability*.—Viable.

Use: Dessert. Market — local and long distance.

Keeping quality: Good, held firm in cold storage 2 weeks with minimal loss of flavor, firmness or internal flesh breakdown.

Shipping quality: Good, minimal scarring of skin or bruising of flesh during picking, packing and shipping trials.

Plant disease resistance/susceptibility: No specific testing for relative plant/fruit disease has been designed. Under close observation during planting, growing and harvesting of fruit, under normal cultural and growing conditions near Modesto, Calif., no particular plant/fruit disease resistance or susceptibility has been observed. Any variety or selection observed during indexing of plant characteristics with abnormal susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of nectarine tree, substantially as illustrated and described, characterized by its large size, upright growth and being a productive and regular bearer of large, yellow flesh, clingstone fruit with good flavor and eating quality; the tree is further characterized by having a low winter chilling requirement of approximately 300 hours and, compared with fruit of the 'May Glo' Nectarine (U.S. Plant Pat. No. 5,245), the fruit is larger in size and is approximately 6 days earlier in maturity.

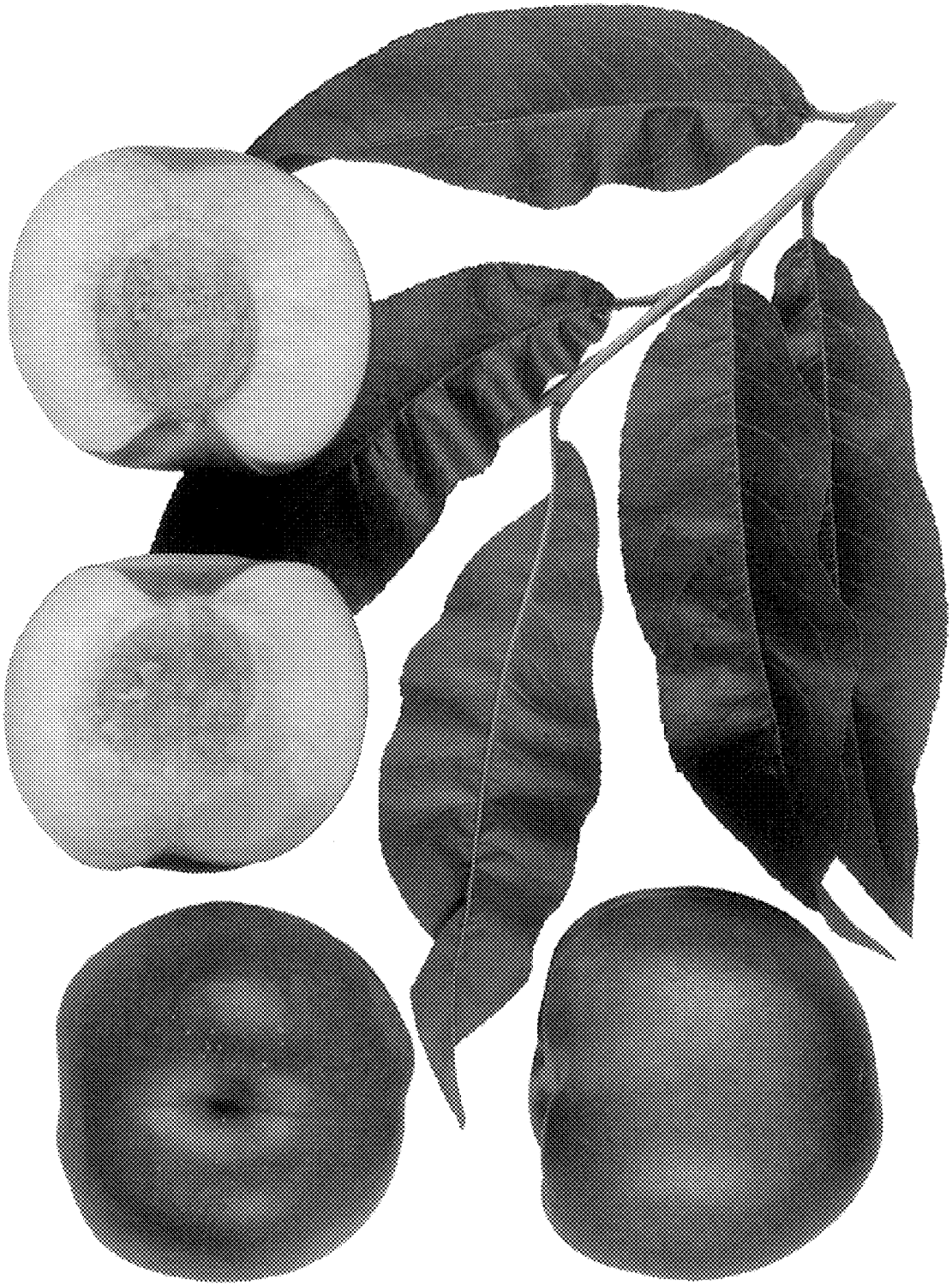

* * * * *